United States Patent
Slaga et al.

(10) Patent No.: US 11,642,354 B2
(45) Date of Patent: *May 9, 2023

(54) METHODS AND COMPOSITIONS COMPRISING URSOLIC ACID AND/OR RESVERATROL FOR TREATING DIABETES, OR CANCER

(71) Applicant: Board of Regents, the University of Texas System

(72) Inventors: Thomas J. Slaga, San Antonio, TX (US); Jacob Junco, San Antonio, TX (US); Huiyun Liang, San Antonio, TX (US); Sara Reyna, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/233,456

(22) Filed: Apr. 17, 2021

(65) Prior Publication Data

US 2022/0226347 A1 Jul. 21, 2022

Related U.S. Application Data

(63) Continuation of application No. 16/918,378, filed on Jul. 1, 2020, now Pat. No. 11,090,311, which is a continuation of application No. 16/813,017, filed on Mar. 9, 2020, now Pat. No. 11,166,962, which is a continuation of application No. 16/221,094, filed on Dec. 14, 2018, now Pat. No. 10,583,145, which is a continuation of application No. 15/308,427, filed as application No. PCT/US2015/029224 on May 5, 2015, now Pat. No. 10,155,003.

(60) Provisional application No. 61/988,859, filed on May 5, 2014.

(51) Int. Cl.
| | |
|---|---|
| A61K 31/56 | (2006.01) |
| A61K 31/19 | (2006.01) |
| A61K 31/05 | (2006.01) |
| A61P 3/04 | (2006.01) |
| A61P 3/10 | (2006.01) |
| A61K 9/00 | (2006.01) |

(52) U.S. Cl.
CPC ............ A61K 31/56 (2013.01); A61K 9/0053 (2013.01); A61K 31/05 (2013.01); A61K 31/19 (2013.01); A61P 3/04 (2018.01); A61P 3/10 (2018.01)

(58) Field of Classification Search
None
See application file for complete search history.

(56) References Cited

U.S. PATENT DOCUMENTS

| | | | | |
|---|---|---|---|---|
| 7,772,195 B2 | 8/2010 | Nair et al. | | 514/27 |
| 10,155,003 B2* | 12/2018 | Slaga | | A61K 31/19 |
| 10,583,145 B2* | 3/2020 | Slaga | | A61K 31/56 |
| 11,090,311 B2* | 8/2021 | Slaga | | A61K 31/05 |
| 11,166,962 B2* | 11/2021 | Slaga | | A61K 31/19 |
| 2012/0165412 A1 | 6/2012 | Van der Beek | | 514/733 |
| 2021/0252016 A1* | 8/2021 | Slaga | | A61P 3/04 |
| 2022/0023241 A1* | 1/2022 | Slaga | | A61P 11/00 |

FOREIGN PATENT DOCUMENTS

WO  WO/14/014530  1/2014

OTHER PUBLICATIONS

"Consuming." Merriam-Webster.com Dictionary, Merriam-Webster, https://www.merriam-webster.com/dictionary/consuming. Accessed Sep. 27, 2022. (Year: 2022).*
"Consuming." Google.com, https://www.google.com/search?q=consuming+definition&source. Accessed Sep. 27, 2022. (Year: 2022).*
Al-Abd et al. "Resveratrol enhances the cytotoxic profile of docetaxel and doxorubicin in solid tumour cell lines in vitro," *Cell Prolif.*, 2011, vol. 44, No. 6, pp. 591-601.
Aziz et al. "Chemoprevention of skin cancer by grape constituent resveratrol: relevance to human disease?" *FASEB J*, 2005, vol. 19, No. 9, 19 pages.
Baird et al. "Carcinogenic polycyclic aromatic hydrocarbon-DNA adducts and mechanism of action," *Eniron. Mol. Mutagen.* 2005, vol. 45, Nos. 2-3, pp. 106-114.
Barr et al. *Circulation*. 2007, 116(2):151-157.
Bauche et al. "Overexpression of adiponectin targeted to adipose tissue in transgenic mice: impaired adipocyte differentiation," *Endocrinology*. 2007, vol. 148, No. 4, pp. 1539-1549.
Baur et al. *Nature* 2006, 444(7117):337-342.
Birk and Wojtaszewski. *J Physiol* 2006, 577(Pt 3):1021-1032.
Boffetta et al, "Cancer risk from occupational and environmental exposure to polycyclic aromatic hydrocarbons." *Cancer Causes Control*. 1997, vol. 8, No. 3, pp. 444-472.
Boscoe and Schymura. *BMC Cancer*. 2006 6:264.
Brasnyó et al. "Resveratrol improves insulin sensitivity, reduces oxidative stress and activates the Akt pathway in type 2 diabetic patients." *Br J Nutr*., 2011, vol. 106, No. 3, pp. 383-389.
Chen et al. "Secretion of adiponectin by human placenta: differential modulation of adiponectin and its receptors by cytokines." *Diabetalogica*. 2006, vol. 49, No. 6, pp. 1292-1302.
Chen et al. *EMBO J* 2002, 21(23):6539-6548.
Chen et al. *Mol Cell Biol* 2005, 25(18):7966-7975.
Cherniack. "Polyphenols: planting the seeds of treatment for the metabolic syndrome." *Nutrition*, 2011, vol. 27, No. 6, pp. 617-623.
Coppola et al, "Effect of weight loss on coronary circulation and adiponectin levels in obese women," *Int J Cardiol*. 2008, vol. 134, No. 3, pp. 414-416.
Diez et al. "The role of the novel adipocyte-derived hormone adiponectin in human disease." *Eur J Endocrinol*. 2003, vol. 148, No. 3, pp. 293-300.
Faubert et al. *Cell Metab* 2013, 17(1):113-124.

(Continued)

*Primary Examiner* — My-Chau T. Tran

(57) ABSTRACT

Certain embodiments are directed to methods and compositions for treating obesity, diabetes, and/or cancer with a combination of ursolic acid and resveratrol.

18 Claims, 4 Drawing Sheets

(56) References Cited

OTHER PUBLICATIONS

Frentz et al. "Malignant tumours and psoriasis: a follow-up study." *Br. J. Dermatol.* 1999, vol. 140, No. 2, pp. 237-242.
Gialeli et al. *FEBS J.* 2011, 278(1):16-27.
Graf et al. *Curr Opin Investig Drugs* 2010, 11(10):1107-1115.
Hardie et al. "AMP-activated protein kinase: a target for drugs both ancient and modern." *Chem Biol* 2012, vol. 19, No. 10, pp. 1222-1236.
Hattori et al. *Hypertension* 2006, 47(6):1183-1188.
Hoene et al. *J Physiol* 2009, 587(Pt 1):241-252.
Hsing et al. *PLoS One* 2011, 6(3):e17598.
Huang et al. "Important role of the LKB1-AMPK pathway in suppressing tumorigenesis in PTEN-deficient mice." *Biochem J* 2008, vol. 412, No. 2, pp. 211-221.
Huang et al. *Cancer Res* 1994, 54(3):701-708.
Ibiebele et al. *Am J Clin Nutr* 2007, 85(5):1401-1408.
International Preliminary Report on Patentability in International Application No. PCT/US2015/029224 dated Nov. 8, 2016.
International Search Report and Written Opinion in International Application No. PCT/US2015/029224 dated Jul. 23, 2015.
Jang et al. "Ursolic acid enhances the cellular immune system and pancreatic beta-cell function in streptozotocin-induced diabetic mice fed a high-fat diet." *Int Immunopharmacol* 2009, vol. 9, No. 1, pp. 113-119.
Junco, et al., "Resveratrol and P-glycoprotein inhibitors enhance the anti-skin cance effects of ursolic acid." Mol Cancer Res. 11(12):1-17, 2013.
Kahn et al. "Increased cancer mortality following a history of nonmelanoma skin cancer." *JAMA.* 1998, vol. 280, No. 10, pp. 910-912.
Kapadia et al. "Chemopreventive effect of resveratrol, sesamol, sesame oil and sunflower oil in the Epstein-Barr virus early antigen activation assay and the mouse skin two-stage carcinogenesis." *Pharmacol Res* 2002, vol. 45, No. 6, pp. 499-505.
Kato et al. "CK2 Is a C-Terminal IkappaB Kinase Responsible for NF-kappaB Activation during the UV Response." *Mol Cell* 2003, vol. 12, No. 4, pp. 829-839.
Khafif et al. "Quantitation of chemopreventive synergism between (−)-epigallocatechin-3-gallate and curcumin in normal, premalignant and malignant human oral epithelial cells." *Carcinogenesis* 1998, vol. 19, No. 3, pp. 419-424.
Kiernan et al. *J Biol Chem* 2003, 278(4):2758-2766.
Kimura et al. "Inhibitory effects of polyphenols on human cytochrome P450 3A4 and 2C9 activity." *Food Chem Toxicol* 2010, vol. 48, No. 1, pp. 429-435.
Koopman et al. *Am J Physiol Endocrinol Metab* 2006, 290(6):E1245-1252.
Krueger et al. "Burden of Malignancy After a Primary Skin Cancer: Recurrence, Multiple Skin Cancers and Second Primary Cancers." *Can. J. Public Health.* 2010, vol. 101, No. 4, pp. 123-127.
Kundu et al. "Inflammation: gearing the journey to cancer." *Mutat Res* 2008, vol. 659, Nos. 1-2, pp. 15-30.
Laszlo et al. *Photochem Photobiol* 2008, 84(6):1564-1568.
Lea et al. "Ambient UVB and melanoma risk in the United States: a case-control analysis." *Ann. Epidemiol.* 2007, vol. 17, No. 6, pp. 447-453.
Leiherer et al. "Phytochemicals and their impact on adipose tissue inflammation and diabetes." *Vascul Pharmacol* 2013, vol. 58, Nos. 1-2, pp. 3-20.
Long et al. *Clin. Gastroenterol. Hepatol.* 2010, 8(3):268-274.
Lu et al. "Inhibition of prostate cancer cell growth by an avocado extract: role of lipid-soluble bioactive substances." *J Nutr Biochem* 2005, vol. 16, No. 1, pp. 23-30.
Musi et al. *Diabetes* 2002, 51(7):2074-2081.
Nichols et al. *Diabetes Care.* 2007, 30(2):228-233.

Quan et al. "Reversal effect of resveratrol on multidrug resistance in KBv200 cell line." *Biomed Pharmacother* 2008, vol. 62, No. 9, pp. 622-629.
Rajendrasozhan et al. *Pulm Pharmacol Ther* 2010, 23(3):172-181.
Renaldi et al. "Hypoadiponectinemia: a risk factor for metabolic syndrome." *Acta Med Indones.* 2009, vol. 41, No. 1, pp. 20-24.
Rogers et al. "Incidence estimate of nonmelanoma skin cancer in the United States, 2006." *Arch. Dermatol.* 2010, vol. 146, No. 3, pp. 283-287.
Saw et al. *Biopharm Drug Dispos* 2011, 32(5):289-300.
Shan et al. "Proliferation-inhibiting and apoptosis-inducing effects of ursolic acid and oleanolic acid on multi-drug resistance cancer cells in vitro." *Chin J Integr Med* 2011, vol. 17, No. 8, pp. 607-611.
Shi et al. "A novel indirubin derivative PHII-7 potentiates adriamycin cytotoxicity via inhibiting P-glycoprotein expression in human breast cancer MCF-7/ADR cells." *Eur J Pharmacol* 2011, vol. 669, Nos. 1-3, pp. 38-44.
Somova et al. "Cardiovascular, antihyperlipidemic and antioxidant effects of oleanolic and ursolic acids in experimental hypertension." *Phytomedicine* 2003, vol. 10, Nos. 2-3, pp. 115-121.
Son et al. "Activation of AMP-activated protein kinase and phosphorylation of glycogen synthase kinase3 β mediate ursolic acid induced apoptosis in HepG2 liver cancer cells." *Phytother Res* 2013, vol. 27, No. 11, pp. 1714-1722.
Suganuma et al. *Cancer Res* 1999, 59(1):44-47.
Taesotikul et al. *Drug Metab Pharmacokinet* 2011, 26(2):154-161.
Timmers et al. *Cell Metab* 2011, 14(5):612-622.
Tokuda et al. "Inhibitory effects of ursolic and oleanolic acid on skin tumor promotion by 12-O-tetradecanoylphorbol-13-acetate." *Cancer Lett* 1986, vol. 33, No. 3, pp. 279-285.
Tomizawa et al. "Fenofibrate suppresses microvascular inflammation and apoptosis through adenosine monophosphate-activated protein kinase activation." *Metabolism* 2011, vol. 60, No. 4, pp. 513-522.
Tsurutani et al. "Tobacco components stimulate Akt-dependent proliferation and NFkappaB-dependent survival in lung cancer cells." *Carcinogenesis* 2005, vol. 26, No. 7, pp. 1182-1195.
Ukkola et al. "Adiponectin: a link between excess adiposity and associated comorbidities?" *J Mol Med.* 2002, vol. 80, No. 11, pp. 696-702.
Um et al. *Diabetes* 2010, 59(3):554-563.
Xia et al. *J Diabetes* 2010, 2(4):243-249.
Xu et al. "Resveratrol role in cardiovascular and metabolic health and potential mechanisms of action," *Nutr Res* 2012, vol. 32, No. 9, pp. 648-658.
Yamauchi et al. "The fat-derived hormone adiponectin reverses insulin resistance associated with both lipoatrophy and obesity." *Nat Med.* 2001, vol. 7, No. 8, pp. 941-946.
Zhang et al. "Glycomic alterations are associated with multidrug resistance in human leukemia." *Int J Biochem Cell Biol* 2012, vol. 44, No. 8, pp. 1244-1253.
Zheng et al. "Ursolic acid-induced AMP-activated protein kinase (AMPK) activation contributes to growth inhibition and apoptosis in human bladder cancer T24 cells." *Biochem Biophys Res Commun* vol. 419, No. 4, 2012, pp. 741-747.
Zhou et al. *J Clin Invest* 2001, 108(8):1167-1174.
Jung and Chong, "The management of obesity" Clin Endocrinol. 35:11-20, 1991.
Lee et al. "Radix clematidis extract inhibits UVB-induced MMP expression by suppressing the NF-kb pathway in human dermal fibroblasts" Int J Molec Med. 23:679-84, 2009.
Mendez-del Villar, et al. "Effect of resveratrol administration on metabolic syndrome, insulin sensitivity, and insulin secretion" Metab Syndrome and Related Disorders. 12(10):497-502, 2014.
Kune, et al., "Diet, alcohol, smoking, serum beta-carotene and vitamin A in male nonmelanocytic skin cancer patients and controls" Nutr and Cancer. 18:237-44, 1992.

* cited by examiner

METHODS AND COMPOSITIONS COMPRISING URSOLIC ACID AND/OR RESVERATROL FOR TREATING DIABETES, OR CANCER

RELATED APPLICATIONS

This application is a continuation of U.S. application Ser. No. 16/918,378 filed Jul. 1, 2020; which is a continuation of U.S. application Ser. No. 16/813,017 filed Mar. 9, 2020, which is a continuation of application Ser. No. 16/221,094 filed Dec. 14, 2018 (now U.S. Pat. No. 10,583,145), which is a continuation of application Ser. No. 15/308,427 (now U.S. Pat. No. 10,155,003) filed Nov. 2, 2016, which is a national phase application under 35 USC § 371 of International Application No. PCT/US2015/029224 filed May 5, 2015, which claims priority to U.S. Provisional Application No. 61/988,859 filed May 5, 2014, each of which is hereby incorporated in their entirety.

STATEMENT REGARDING FEDERALLY FUNDED RESEARCH

This invention was made with government support under CA54174 awarded by the National Institutes of Health. The government has certain rights in the invention.

BACKGROUND

The recent explosion of obesity, type II diabetes, heart disease, and some cancers in the United States can be largely attributed to two key well-known factors, a lack of a healthy diet and reduced physical activity. Type II diabetes, high blood pressure, and heart disease are components of the "metabolic syndrome", an umbrella term for maladies typically developed as a consequence of being overweight/obese and physically inactive. Studies have shown that physical activity and reduced calorie intake, or "calorie restriction" inhibit degenerative and chronic disease, especially those of the metabolic syndrome and cancer.

Obesity is a chronic disease that is prevalent in modern society and is associated not only with a social stigma, but also with decreased life span and numerous medical problems—obesity is a primary risk factor for type II diabetes mellitus and is a strong risk factor for cardiovascular disease and cancer as well. Much of this obesity-induced pathology can be attributed to the strong association with dyslipidemia, hypertension, and insulin resistance. Many studies have demonstrated that reduction in obesity by diet and exercise reduces these risk factors dramatically. Unfortunately these treatments are largely unsuccessful with a failure rate reaching 95%. This failure may be due to the fact that the condition is strongly associated with genetically inherited factors that contribute to increased appetite, preference for highly caloric foods, reduced physical activity, and increased lipogenic metabolism. This indicates that people inheriting these genetic traits are prone to becoming obese regardless of their efforts to combat the condition.

Existing therapies for obesity include standard diets and exercise, very low calorie diets, behavioral therapy, pharmacotherapy involving appetite suppressants, thermogenic drugs, and food absorption inhibitors, mechanical devices such as jaw wiring, waist cords, balloons, and surgery (Jung and Chong. *Clinical Endocrinology*. 1991, 35:11-20; Bray. *Am J Clin Nutr.* 1992, 55:538S-544S). Because dieting and exercise produce only modest results, researchers have searched for a compound to accelerate the loss of body fat. However, of the drugs currently allowed for use over a long time period, sibutramine, an appetite depressant, and orlistat, a lipase inhibitor, have side effects including headaches, polydipsia (serious thirst), insomnia, constipation, hypertension, and increased pulse rate and fecal incontinence, frequent or urgent bowel movements, steatorrhea, and a reduction in the absorption of fat-soluble vitamins, respectively.

There remains a need for additional compositions and methods for the treatment of obesity, diabetes, and various cancers.

SUMMARY

Certain embodiments are directed to methods and compositions for treating obesity, diabetes, and/or cancer with a combination of ursolic acid and resveratrol. Certain embodiments are directed to compositions for supplementing a human diet. Ursolic acid is a phytonutrient found in a wide variety of food products and herbs especially apples, olives, and rosemary. As described herein, studies indicate that ursolic acid administration can mimic and enhance the effects of calorie restriction and exercise. Ursolic acid inhibits chronic inflammation and increases the effectiveness of anti-diabetic drugs such as Rosiglitazone and Metformin on glucose uptake into insulin resistant fat cells. Resveratrol is a phytonutrient found in the skin of red grapes and in other fruits. Resveratrol exerts many of its beneficial effects through its ability to mimic and enhance the effects of calorie restriction and exercise.

Certain embodiments are directed to methods for treating obesity comprising administering an effective amount of ursolic acid and an effective amount of resveratrol to an obese subject. In certain aspects ursolic acid is administered at a dose of between 50, 100, 150, 200, 250, 300 to 250, 300, 350, 400, 450, 500, 550, 600 mg/day, including all values and ranges there between. In certain aspects 50, 100, 150, 200, 250, 300, 350, 400, 450, 500, 550, or 600 mg of ursolic acid is administered. In a further aspect the dose of ursolic acid is administered in one dose or in multiple doses over 0.5, 1, 2, 3, 4, 5, 6, 7, 8, 9, or 10 minutes, hours or days. In certain aspects resveratrol is administered at a dose of between 50, 100, 150, 200, 250, 300 to 250, 300, 350, 400, 450, 500, 550, 600 mg/day, including all values and ranges there between. In certain aspects 50, 100, 150, 200, 250, 300, 350, 400, 450, 500, 550, or 600 mg of resveratrol is administered. In a further aspect the dose of resveratrol is administered in one dose or in multiple doses over 0.5, 1, 2, 3, 4, 5, 6, 7, 8, 9, or 10 minutes, hours or days. In certain aspects ursolic acid and resveratrol are administered at a ratio of 4:1, 3:1, 2:1, 1:1, 1:2, 1:3, or 1:4, including all values and ranges there between. In certain aspects ursolic acid and resveratrol are administered individually. Individual administration refers to the compounds being formulated is separate formulations. The compounds when administered individually can be administered at the same time or within about 1, 2, 3, 4, 5, 6, 7, 8, 9, or 10 minutes, hours, or days. In certain aspects ursolic acid and resveratrol are formulated in the same composition. Ursolic acid and/or resveratrol can be formulated as a tablet, a capsule, a concentrate, a powder, a beverage, a baked good, chocolate, caramel, cookie, bar, and/or snack. In certain aspects ursolic acid and/or resveratrol are administered orally.

In certain aspects administration of ursolic acid is prior to administration of resveratrol. In a further aspect administration of ursolic acid is concurrent with resveratrol. In still a further aspects administration of resveratrol is prior to administration of ursolic acid.

In certain aspects ursolic acid and resveratrol are administered to a subject having a body mass index (BMI) of 25, 30, 40, 50, or greater. The subject can be diagnosed with pre-diabetes.

Certain embodiments are directed to methods and compositions for treating diabetes comprising administering an effective amount of ursolic acid in combination with an effective amount of resveratrol to the subject. In certain aspects ursolic acid is administered at a dose of between 50, 100, 150, 200, 250, 300 to 250, 300, 350, 400, 450, 500, 550, 600 mg/day, including all values and ranges there between. In certain aspects 50, 100, 150, 200, 250, 300, 350, 400, 450, 500, 550, or 600 mg of ursolic acid is administered. In a further aspect the dose of ursolic acid is administered in one dose or in multiple doses over 0.5, 1, 2, 3, 4, 5, 6, 7, 8, 9, or 10 minutes, hours or days. In certain aspects resveratrol is administered at a dose of between 50, 100, 150, 200, 250, 300 to 250, 300, 350, 400, 450, 500, 550, 600 mg/day, including all values and ranges there between. In certain aspects 50, 100, 150, 200, 250, 300, 350, 400, 450, 500, 550, or 600 mg of resveratrol is administered. In a further aspect the dose of resveratrol is administered in one dose or in multiple doses over 0.5, 1, 2, 3, 4, 5, 6, 7, 8, 9, or 10 minutes, hours or days. In certain aspects ursolic acid and resveratrol are administered at a ratio of 4:1, 3:1, 2:1, 1:1, 1:2, 1:3, or 1:4, including all values and ranges there between. In certain aspects ursolic acid and resveratrol are administered individually. Individual administration refers to the compounds being formulated is separate formulations. The compounds when administered individually can be administered at the same time or within about 1, 2, 3, 4, 5, 6, 7, 8, 9, or 10 minutes, hours, or days. In certain aspects ursolic acid and resveratrol are formulated in the same composition. Ursolic acid and/or resveratrol can be formulated as a tablet, a capsule, a concentrate, a powder, a beverage, a baked good, chocolate, caramel, cookie, bar, and/or snack. In certain aspects ursolic acid and/or resveratrol are administered orally.

In certain aspects administration of ursolic acid is prior to administration of resveratrol. In a further aspect administration of ursolic acid is concurrent with resveratrol. In still a further aspects administration of resveratrol is prior to administration of ursolic acid.

Certain embodiments are directed to methods and compositions for treating pre-diabetes comprising administering an effective amount of ursolic acid in combination with an effective amount of resveratrol to a subject. In certain aspects ursolic acid is administered at a dose of between 50, 100, 150, 200, 250, 300 to 250, 300, 350, 400, 450, 500, 550, 600 mg/day, including all values and ranges there between. In certain aspects 50, 100, 150, 200, 250, 300, 350, 400, 450, 500, 550, or 600 mg of ursolic acid is administered. In a further aspect the dose of ursolic acid is administered in one dose or in multiple doses over 0.5, 1, 2, 3, 4, 5, 6, 7, 8, 9, or 10 minutes, hours or days. In certain aspects resveratrol is administered at a dose of between 50, 100, 150, 200, 250, 300 to 250, 300, 350, 400, 450, 500, 550, 600 mg/day, including all values and ranges there between. In certain aspects 50, 100, 150, 200, 250, 300, 350, 400, 450, 500, 550, or 600 mg of resveratrol is administered. In a further aspect the dose of resveratrol is administered in one dose or in multiple doses over 0.5, 1, 2, 3, 4, 5, 6, 7, 8, 9, or 10 minutes, hours or days. In certain aspects ursolic acid and resveratrol are administered at a ratio of 4:1, 3:1, 2:1, 1:1, 1:2, 1:3, or 1:4, including all values and ranges there between. In certain aspects ursolic acid and resveratrol are administered individually. Individual administration refers to the compounds being formulated is separate formulations. The compounds when administered individually can be administered at the same time or within about 1, 2, 3, 4, 5, 6, 7, 8, 9, or 10 minutes, hours, or days. In certain aspects ursolic acid and resveratrol are formulated in the same composition. Ursolic acid and/or resveratrol can be formulated as a tablet, a capsule, a concentrate, a powder, a beverage, a baked good, chocolate, caramel, cookie, bar, and/or snack. In certain aspects ursolic acid and/or resveratrol are administered orally.

In certain aspects administration of ursolic acid is prior to administration of resveratrol. In a further aspect administration of ursolic acid is concurrent with resveratrol. In still a further aspects administration of resveratrol is prior to administration of ursolic acid.

Still further embodiments are directed to compositions and methods for treating skin cancer comprising administering an effective amount of ursolic acid in combination with an effective amount of resveratrol. In certain aspects ursolic acid is administered at a dose of between 50, 100, 150, 200, 250, 300 to 250, 300, 350, 400, 450, 500, 550, 600 mg/day, including all values and ranges there between. In certain aspects 50, 100, 150, 200, 250, 300, 350, 400, 450, 500, 550, or 600 mg of ursolic acid is administered. In a further aspect the dose of ursolic acid is administered in one dose or in multiple doses over 0.5, 1, 2, 3, 4, 5, 6, 7, 8, 9, or 10 minutes, hours or days. In certain aspects resveratrol is administered at a dose of between 50, 100, 150, 200, 250, 300 to 250, 300, 350, 400, 450, 500, 550, 600 mg/day, including all values and ranges there between. In certain aspects 50, 100, 150, 200, 250, 300, 350, 400, 450, 500, 550, or 600 mg of resveratrol is administered. In a further aspect the dose of resveratrol is administered in one dose or in multiple doses over 0.5, 1, 2, 3, 4, 5, 6, 7, 8, 9, or 10 minutes, hours or days. In certain aspects ursolic acid and resveratrol are administered at a ratio of 4:1, 3:1, 2:1, 1:1, 1:2, 1:3, or 1:4, including all values and ranges there between. In certain aspects ursolic acid and resveratrol are administered individually. Individual administration refers to the compounds being formulated is separate formulations. The compounds when administered individually can be administered at the same time or within about 1, 2, 3, 4, 5, 6, 7, 8, 9, or 10 minutes, hours, or days. In certain aspects ursolic acid and resveratrol are formulated in the same composition. Ursolic acid and/or resveratrol can be formulated as a topical solution (crème, ointment, gel, etc.), tablet, a capsule, a concentrate, a powder, a beverage, a baked good, chocolate, caramel, cookie, bar, and/or snack. In certain aspects ursolic acid and/or resveratrol are administered topically. In certain aspects ursolic acid and/or resveratrol are administered orally.

In certain aspects administration of ursolic acid is prior to administration of resveratrol. In a further aspect administration of ursolic acid is concurrent with resveratrol. In still a further aspects administration of resveratrol is prior to administration of ursolic acid.

The term "isolated" can refer to a compound that is substantially free of cellular material, bacterial material, viral material, culture medium (when produced by recombinant DNA techniques), chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel.

Other embodiments of the invention are discussed throughout this application. Any embodiment discussed with respect to one aspect of the invention applies to other aspects of the invention as well and vice versa. Each embodiment described herein is understood to be an embodiment of the invention that is applicable to other aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

(FIG. 3A) MT1/2 cells co-treated with UA and RES had lower $IC_{50}$ values relative to treatment with UA alone. (FIG. 3B) Ca3/7 cells co-treated with UA and RES had lower $IC_{50}$ values relative to treatment with UA alone. (For A and B, n=3 and * indicates p<0.05 between UA+veh and UA+50 µM RES, $ indicates p<0.05 between UA+veh and UA+100 µM RES).

DESCRIPTION

Figure 1:
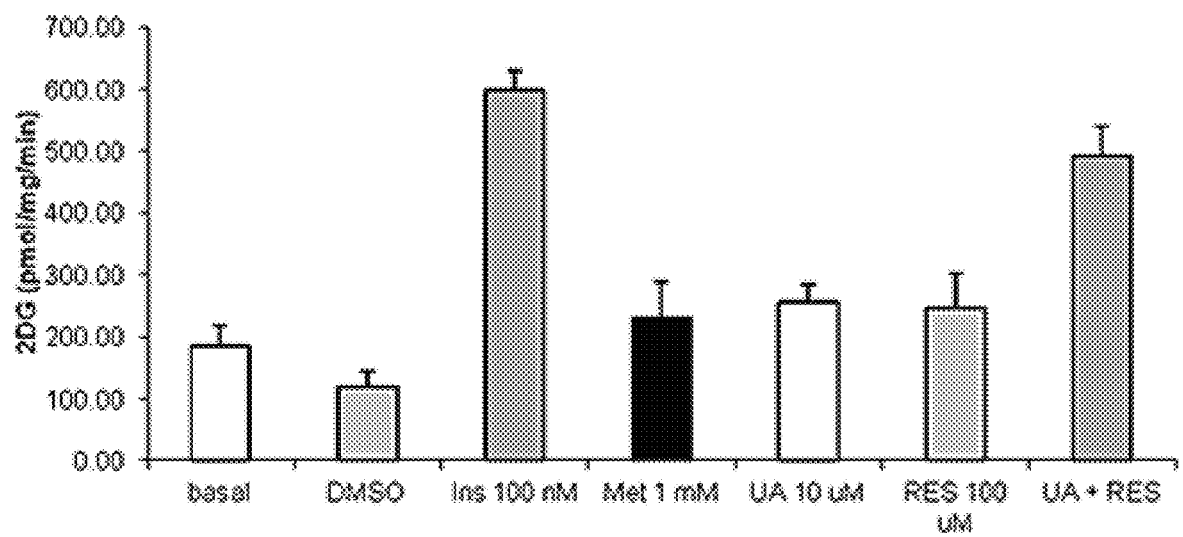
FIG. 1. Ursolic acid (UA) and resveratrol (RES) synergistically increase cellular glucose uptake.

Certain embodiments are directed to treating obesity, diabetes, and cancer with a combination of ursolic acid and resveratrol. Ursolic acid inhibits chronic inflammation. In diabetic rats, dietary ursolic acid decreases resting glucose levels, and improves glucose tolerance and insulin sensitivity. Also, in a rat model of hypertension, ursolic acid decreases blood pressure, resting glucose, LDL cholesterol, and triglycerides to near control levels. Furthermore, mice fed a high-fat diet containing ursolic acid showed a decrease in body weight, normalized glucose levels, an elevated level of circulating insulin, and a dramatic decrease in liver lipids compared to the control mice which became obese and diabetic. These results suggest that ursolic acid has the potential to reduce the risk of obesity and diabetes. In addition ursolic acid increases the effectiveness of anti-diabetic drugs such as Rosiglitazone and Metformin on glucose uptake into insulin resistant fat cells. Ursolic acid is able to reduce fat accumulation and increase muscle mass gain when in a fed state and to induce fat burning and preserve muscle mass when in a fasted stated. In experimental animals ursolic acid also is effective in preventing the induction of skin, breast, prostate, and colon cancer throughout its anti-inflammatory effect.

Resveratrol is a phytonutrient found in the skin of red grapes and in other fruits. Like ursolic acid, it also exerts many of its beneficial effects through its ability to mimic calorie restriction and exercise. The effects of resveratrol are currently a topic of numerous animal and human studies. In experimental animal studies, resveratrol has been shown to have anti-inflammatory, blood sugar lowering, and other beneficial cardiovascular effects. Resveratrol inhibited weight gain in rats fed atherogenic diet (1% cholesterol) with an accompanying decrease in liver inflammation. With regards to the metabolic syndrome, resveratrol improves insulin sensitivity in mice fed a high calorie diet. In type II diabetic humans, insulin sensitivity was improved by the fourth week following daily resveratrol intake. However, while several human studies have reported generally positive effects, resveratrol may have lesser benefits except at very high doses. Like ursolic acid, resveratrol appears to enhance the activity of anti-diabetic drugs. In addition, resveratrol has been shown to inhibit the induction of skin and breast cancer.

Animal studies using either ursolic acid or resveratrol show the same positive effects—preventing obesity, diabetes, and cancer. Recently the inventors have found that a combination of both ursolic acid and resveratrol has very potent synergistic effects on several critical diagnostic markers related to obesity, type II diabetes, and cancer. Recent results show that ursolic acid and resveratrol interact synergistically to dramatically and significantly increase the energy-sensing pathways (AMPK) and decrease the MTOR pathway. Both calorie restriction and exercises have strong effects on these pathways. In addition, a combination of ursolic acid and resveratrol strongly and significantly decreases the inflammatory pathway (NFKB) in the liver and pancreas induced by high fat diets. Both ursolic acid and resveratrol also synergistically increase glucose transport into muscle cells and increase adiponectin secretion from fat cells in diabetic experimental animals. Both of these activities counteract insulin resistance, obesity, and diabetes. The inventors have also found that ursolic acid and resveratrol can synergistically inhibit the inflammatory pathway in human monocytes treated to increase the activity of this pathway. Also, a combination of ursolic acid and resveratrol has an even greater effect when given with a partial calorie restriction and moderate exercise.

I. PRE-DIABETES SYNDROME

Pre-diabetes is the state in which some but not all of the diagnostic criteria for diabetes are met, including impaired fasting glycemia or impaired fasting glucose (IFG) and impaired glucose tolerance (IGT). IFG refers to a condition in which the fasting blood glucose is elevated above what is considered normal levels but is not high enough to be classified as diabetes mellitus. Fasting blood glucose levels are in a continuum within a given population, with higher fasting glucose levels corresponding to a higher risk for complications caused by the high glucose levels. IFG is defined as a fasting glucose that is higher than the upper limit of normal, but not high enough to be classified as diabetes mellitus. Some patients with impaired fasting glucose can also be diagnosed with IGT as described below, but many have normal responses to a glucose tolerance test.

IFG is considered a pre-diabetic state, associated with insulin resistance, increased mortality, and increased risk of cardiovascular pathology, although of lesser risk than IGT (Barr et al. *Circulation*. 2007, 116(2):151-157). There is a 50% risk over 10 years of progressing to overt diabetes, but many newly identified IFG patients progress to diabetes in less than three years (Nichols et al. *Diabetes Care*. 2007, 30(2):228-233).

IGT is a pre-diabetic state of dysglycemia, that is associated with insulin resistance and increased risk of cardiovascular pathology. IGT may precede type 2 diabetes mellitus by many years. IGT is also a risk factor for mortality (Nichols et al. *Diabetes Care*. 2007, 30(2):228-233).

Following the ADA criteria, pre-diabetes can be diagnosed with a blood test with any of the following results: (1) Fasting blood sugar (glucose) level from 100-125 mg/dL (5.6-6.9 mM); (2) A blood sugar level of 140 to 199 mg/dL (7.8 to 11.0 mM) two hours after ingesting the standardized 75 gram glucose solution in the glucose tolerance test; (3) Glycated hemoglobin between 5.7 and 6.4%.

Diabetes can be diagnosed with a blood test with any of the following results: (1) Fasting blood sugar (glucose) level ≥126 mg/dL (7.0 mM); (2) A blood sugar level ≥200 mg/dL (11.1 mM) two hours after ingesting the standardized 75 gram glucose solution in the glucose tolerance test; (3) Glycated hemoglobin ≥6.5%; (4) Symptoms of hyperglycemia and casual plasma glucose ≥200 mg/dL (11.1 mM).

II. OBESITY

Obesity refers to a condition where excessive fat accumulates within the body. In general, when a person's body mass index (BMI) is greater than 30, they are diagnosed as obese. Body mass index (BMI) is a widely used method for estimating body fat mass and is an accurate reflection of body fat percentage in the majority of the adult population. BMI is calculated by dividing the subject's mass by the square of his or her height, typically expressed either in metric or US "Customary" units as $kg/m^2$ or pounds×703/inches. A person with a BMI of 30.0 or greater is defined as obese, with higher BMI values being further classified as severe obesity (35.0 to 40), morbid obesity (40.0 to 45), and super obese (BMI ≥45).

Obesity is caused by an energy imbalance over a long period when an excessive amount of calories are ingested with respect to the amount of energy being expended. Treatment of obesity normally requires behavior therapy as well as a reduction of calories ingested and/or an increase in the amount of calories expended.

Low levels of the protein adiponectin have been associated with a higher risk of developing metabolic syndromes such as obesity. In certain aspects the methods described herein result in the upregulation of adiponectin. Adiponectin (also referred to as GBP-28, apM1, AdipoQ and Acrp30) is a 244 amino acid protein that in humans is encoded by the ADIPOQ gene. It is a protein hormone that modulates a number of metabolic processes, including glucose regulation and fatty acid oxidation. Adiponectin is secreted into the bloodstream from adipose tissue and also from the placenta in pregnancy (Chen et al. *Diabetalogica*. 2006, 49(6):1292-1302). In the bloodstream, adiponectin accounts for approximately 0.01% of all plasma protein at around 5-10 μg/mL and is very abundant in plasma relative to many hormones. Levels of the hormone are inversely correlated with body fat percentage in adults, while the association in infants and young children is less clear (Ukkola and Santaniemi. *J Mol Med*. 2002, 80(11):696-702).

Transgenic mice with increased adiponectin show impaired adipocyte differentiation and increased energy expenditure associated with protein uncoupling (Bauche et al. *Endocrinology*. 148(4):1539-1549). The hormone plays a role in the suppression of the metabolic derangements that may result in type 2 diabetes, obesity, atherosclerosis, non-alcoholic fatty liver disease (NAFLD) and an independent risk factor for metabolic syndrome (Diez and Iglesias. *Eur J Endocrinol*. 2003, 148(3):293-300; Ukkola and Santaniemi. *J Mol Med*. 2002, 80(11):696-702; Renaldi et al. *Acta Med Indones*. 2009, 41(1):20-24). Adiponectin in combination with leptin has been shown to completely reverse insulin resistance in mice (Yamauchi et al. *Nat Med*. 2001, 7(8):941-946). Levels of adiponectin are reduced in diabetics compared to non-diabetics. Weight reduction significantly increases circulating levels (Coppola et al, *Int J Cardiol*. 2008 134(3):414-416).

III. SKIN CANCER

There are over one million new cases of skin cancer diagnosed in the United States each year (Rogers et al. *Arch. Dermatol*. 2010, 146(3):283-287). In addition, skin cancer is associated with a 15-30% increased risk of other forms of cancer (Kahn et al. *JAMA*. 1998 280(10):910-912; Krueger et al. *Can. J Public Health*. 2010, 101(4):123-27). This indicates the importance of mechanisms to prevent or treat skin cancer. Skin cancer consists primarily of melanoma, basal cell carcinoma, and squamous cell carcinoma. Skin cancers have higher risk with increased UV exposure (Boscoe and Schymura. *BMC Cancer*. 2006 6:264; Lea et al. *Ann. Epidemiol*. 2007, 17(6):447-453) and higher prevalence in individuals with inflammatory disorders (Frentz and Olsen. *Br. J Dermatol*. 1999, 140(2):237-242; Long et al. *Clin. Gastroenterol. Hepatol*. 2010, 8(3):268-274).

Cancer develops via three phases: initiation, promotion, and progression. During initiation, DNA mutations lead to activation of oncogenes and inactivation of tumor suppressor genes. DNA mutations in skin cancer are caused by environmental insults such as UV exposure and polycyclic aromatic hydrocarbons (PAHs). PAHs are present in smoke and can form DNA adducts when metabolized (Baird et al *Eniron. Mol. Mutagen*. 2005, 45(2-3):106-144; Boffetta et al, *Cancer Causes Control.* 1997 8(3):444-472). In tumor promotion, activated oncogenes and inactivated tumor suppressor genes cause constitutive activation of tumor-promoting signal transduction pathways. These pathways increase factors for cell proliferation, cell growth, resistance to apoptosis, and angiogenesis (Walaszek et al. *Chest.* 2004, 125(5 Suppl):128S-133 S). Finally, tumor progression occurs when additional genetic alterations allow tumor cells to enter the bloodstream and metastasize to distant organ sites (Gialeli et al. *FEBS J.* 2011, 278(1): 16-27).

The tumor promotion phase is characterized by abnormal activity of many signal transduction pathways, including the nuclear factor kappa B (NFKB) pathway. NFKB is a transcription factor that typically exists as heterodimer of p65 and p50 subunits. A number of tumor-promoting factors including UV light (Kato et al. *Mol Cell* 2003, 12(4):829-839; Lee et al. *Int J Mot Med* 2009, 23(5):679-684) and various tobacco constituents (Rajendrasozhan et al. *Pulm Pharmacol Ther* 2010, 23(3):172-181; Tsurutani et al. *Carcinogenesis* 2005, 26(7):1182-1195) activate the NFKB pathway. These stimuli phosphorylate and activate kinases that phosphorylate the NFKB inhibitor 1 KBa, targeting it for degradation by proteaseomes. Stimuli including UV light (Laszlo and Wu. *Photochem Photobiol* 2008, 84(6):1564-1568), smoke (Rajendrasozhan et al. *Pulm Pharmacol Ther* 2010, 23 (3): 172-181), or inflammatory agents (Hsing et al. *PLoS One* 2011, 6(3):e17598) also phosphorylate the active p65 subunit of NFKB at serines 536 and/or 276, allowing it to recruit histone acetyltransferases (HATs) (Chen et al. *Mol Cell Biol* 2005, 25(18):7966-7975). These HATs acetylate p65 at a number of lysine residues, resulting in dissociation of NFKB from its inhibitor IKBa (Chen et al. *EMBO J* 2002, 21(23):6539-6548; Kiernan et al. *J Blot Chem* 2003, 278 (4):2758-2766). Once free from IKBa, NFKB can translocate to the nucleus where it transcribes factors for cell proliferation, inflammation, resistance to apoptosis, angiogenesis, and metastasis (Kundu and Surh. *Mutat Res* 2008, 659(1-2):15-30).

Certain phytochemicals present in fruits and vegetables can inhibit cancer formation and growth in many experimental models. Also, epidemiological studies show that consumption of phytochemical-rich fruits and vegetables decreases the risk of many cancer types including skin cancer (Ibiebele et al. *Am J Clin Nutr* 2007, 85(5):1401-1408; Kune et al. *Nutr Cancer* 1992, 18(3):237-244). Resveratrol inhibits formation of many tumor types in animal models, including those of the skin (Aziz et al. *FASEB J* 2005, 19(9):1193-1195; Kapadia et al. *Pharmacol Res* 2002, 45(6):499-505). Ursolic acid (UA) also inhibits tumor formation in a number of models including chemically-induced skin cancer (Huang et al. *Cancer Res* 1994, 54(3):701-708; Tokuda et al. *Cancer Lett* 1986, 33(3):279-285). Resveratrol and UA also inhibit NFKB signaling.

In addition to their anti-cancer effects, a wide range of phytochemicals and plant extracts have also been shown to inhibit the metabolic syndrome, including insulin resistance and diabetes (Xia and Weng. *J Diabetes* 2010, 2(4):243-249; Graf et al. *Curr Opin Investig Drugs* 2010, 11(10):1107-1115; Cherniack. *Nutrition* 2011, 27(6):617-623; Leiherer et al. *Vascul Pharmacol* 2013, 58(1-2):3-20). In many cases these effects are associated with AMP-activated kinase (AMPK), which also mediates the activities of prescribed anti-diabetic drugs like metformin (Hattori et al. *Hypertension* 2006, 47(6):1183-1188; Musi et al. *Diabetes* 2002, 51(7):2074-2081; Zhou et al. *J Clin Invest* 2001, 108(8): 1167-1174; Hardie et al. *Chem Biol* 2012, 19(10):1222-1236). AMPK is activated by exercise in humans and animals as indicated by an increase in phosphorylation of threonine 172 (Birk and Wojtaszewski. *J Physiol* 2006, 577(Pt 3):1021-1032; Hoene et al. *J Physiol* 2009, 587(Pt 1):241-252; Koopman et al. *Am J Physiol Endocrinol Metab* 2006, 290(6):E1245-1252). AMPK also plays a key role in NFKB inhibition by different compounds used to treat diabetes (Hattori et al. *Hypertension* 2006, 47(6):1183-1188; Tomizawa et al. *Metabolism* 2011, 60(4):513-522).

Resveratrol and UA improve symptoms of metabolic syndromes and diabetic symptoms in both animal and humans (Baur et al. *Nature* 2006, 444(7117):337-342; Brasnyo et al. *Br J Nutr* 2011, 106(3):383-389; Jang et al. *Int Immunopharmacol* 2009, 9(1):113-119; Somova et al. *Phytomedicine* 2003, 10(2-3):115-121). Resveratrol activates AMPK in many organisms including humans (Timmers et al. *Cell Metab* 2011, 14(5):612-622; Xu and Si. Nutr Res 2012, 32(9):648-658), and the full effects of resveratrol on the metabolic syndrome depend on AMPK activity (Um et al. *Diabetes* 2010, 59(3):554-563). The cytotoxic effects of UA in different cancer cell lines are also dependent on AMPK activation (Son et al. *Phytother Res* 2013; Zheng et al. *Biochem Biophys Res Commun* 2012, 419(4):741-747). Finally, AMPK activity suppresses tumorigenesis in tumor-susceptible animals (Huang et al. *Biochem J* 2008, 412(2): 211-221; Faubert et al. *Cell Metab* 2013, 17(1):113-124). These results indicate the anti-cancer and anti-diabetic effects of many natural compounds like resveratrol and UA may be mediated by AMPK activation.

There are many potential synergistic mechanisms for different phytochemical combinations. One drug may modulate the metabolism of the other (Kimura et al. *Food Chem Toxicol* 2010, 48(1):429-435; Taesotikul et al. *Drug Metab Pharmacokinet* 2011, 26(2):154-161), or impact its ability to enter the bloodstream (Lu et al. *J Nutr Biochem* 2005, 16(1):23-30) or the cell (Suganuma et al. *Cancer Res* 1999, 59(1):44-47). Drugs can also enhance the ability of each other to induce similar downstream effects, many times by acting along different points on cell regulatory systems (Khafif et al. *Carcinogenesis* 1998, 19(3):419-424; Saw et al. *Biopharm Drug Dispos* 2011, 32(5):289-300).

Resveratrol has been shown to synergistically inhibit tumor cell growth through different mechanisms. Resveratrol has been shown to potentiate the cytotoxic effect of doxorubicin and docetaxel in MCF-7 breast cancer cells, and to enhance doxorubicin concentration in other cancer cell lines (Al-Abd et al. *Cell Prolif* 2011; 44(6):591-601). Resveratrol has also been shown to enhance cytotoxic effects of vincristine, paclitaxel, and doxorubicin in drug-resistant human epidermoid carcinoma line KBv200. Resveratrol has also been shown to decrease the expression of anti-apoptotic bcl-2 and drug efflux pump p-glycoprotein in these chemoresistant cells (Quan et al. *Biomed Pharmacother* 2008; 62(9):622-629).

Ursolic acid has been shown to decrease viability of a number of chemoresistant cancer cell types, however the $IC_{50}$ for UA was still lower in the parental cells (Shan et al. *Chin J Integr Med* 2011, 17(8):607-611), which have lower levels of p-glycoprotein (Zhang et al. *Int J Biochem Cell Biol* 2012, 44(8):1244-1253; Shi et al. *Eur J Pharmacol* 2011; 669(1-3):38-44). These results described herein show the effects of UA can be enhanced by compounds such as resveratrol, which subvert traditional resistance phenotypes. The effects of UA and resveratrol were tested in various skin-relevant systems, including in vivo mouse skin, human keratinocytes, and skin cancer cell lines to determine if this combination has a synergistic effect.

IV. FORMULATION AND ADMINISTRATION

Ursolic acid and resveratrol can be administered to a subject either orally, parenterally (e.g., intravenously, intramuscularly, or subcutaneously), intraperitoneally, or locally (for example, powders, ointments or drops). In certain aspects the compounds are provided in a nutritional supplement formulation. A nutritional supplement formulation can be in any form, e.g., liquid, solid, gel, emulsion, powder, tablet, capsule, or gel cap (e.g., soft or hard gel cap). A nutritional supplement formulation typically will include one or more compositions that have been purified, isolated, or extracted (e.g., from plants) or synthesized, which are combined to provide a benefit (e.g., a health benefit in addition to a nutritional benefit) when used to supplement food in a diet.

Compositions suitable for parenteral injection may comprise physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants.

These compositions may also contain adjuvants such as preserving, wetting, emulsifying, and/or dispersing agents. Prevention of microorganism contamination of the compositions can be accomplished by the addition of various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, sesame seed oil, glycerol, tetrahydrofurfuryl alcohol, polyethylene glycols, fatty acid esters of sorbitan, or mixtures of these substances, and the like.

Suspensions, in addition to the active compound(s), may contain suspending agents, as for example, ethoxylated isostearyl alcohols, polyoxyethylene sorbitol or sorbitan esters, microcrystalline cellulose, aluminum metahydroxide, bentonite, agar-agar, or tragacanth, or mixtures of these substances, and the like.

Dosage forms for topical administration of ursolic acid and resveratrol include ointments, powders, sprays and inhalants. The compound(s) are admixed with a physiologically acceptable carrier, and any preservatives, buffers, and/or propellants that may be required.

For the compounds of the present invention, alone or as part of a supplement composition, the doses are between about 1, 100, 200, 300, 400, 500, 600 to 500, 600, 700, 800, 900, 1000 mg, preferably between 200 and 600 mg. In certain aspects, the ratio of ursolic acid to resveratrol can vary between about 4:1, 3:1 2:1, 1:1, 1:2, 1:3 to 1:4. In certain aspects, the compounds are administered 1, 2, 3, 4, 5, 6, 7, 8, 9, or 10 times per day. In certain aspects, the compounds are administered once every 1, 2, 3, 4, 5, 6, or 7 days.

The term "effective amount" means an amount effective, at dosages and for periods of time necessary, to achieve the desired therapeutic or prophylactic result.

An "effective amount" in reference to decreasing cancer cell growth, means an amount capable of decreasing, to some extent, the growth of some cancer or tumor cells. The term includes an amount capable of invoking a growth inhibitory, cytostatic and/or cytotoxic effect and/or apoptosis of the cancer or tumor cells. Effective doses will be easily determined by one of skill in the art and will depend on the severity and course of the disease, the patient's health and response to treatment, the patient's age, weight, height, sex, previous medical history and the judgment of the treating physician.

The term "subject" means animals, such as dogs, cats, cows, horses, sheep, geese, and humans. Particularly preferred patients are mammals, including humans of both sexes.

The terms "treating", "treat" and/or "treatment" include preventative (e.g., prophylactic) and palliative treatment.

V. EXAMPLES

The following examples as well as the figures are included to demonstrate embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A. Example 1—Ursolic Acid and Resveratrol Activate the Insulin and AMPK Signaling Pathways in Skeletal Muscle Skeletal muscle is the major site for glucose uptake induced by insulin. Insulin binds to the insulin receptor on the muscle cell surface, leading to the activation of several cellular kinases, including Akt and Akt substrate 160 (AS160) facilitating the translocation of the glucose transporter GLUT 4 to the surface of the muscle cell. Glucose then enters the muscle cell through GLUT4. In addition, skeletal muscle AMP-activated protein kinase (AMPK) activation promotes glucose uptake and insulin sensitivity. However, muscle of individuals with type 2 diabetes mellitus (T2DM) is resistant to insulin, mainly due to impaired insulin signaling and glucose transport. Much data show the potential anti-diabetogenic and anti-inflammatory properties of phytonutrients, such as ursolic acid (UA) found in apples and berries and resveratrol (RES) found in peanuts and grapes.

The purpose of this study was to investigate whether UA activates the insulin signaling pathway, and whether a combination of UA and RES synergistically activate AMPK, resulting in GLUT 4 translocation and increased glucose uptake in muscle cells. L6 myotubes were incubated with UA (10 µM) at different time points. Ursolic acid induced Akt phosphorylation by 1.8, 1.7, and 1.8 fold increase at 30, 45, and 60 min. Ursolic acid also increased AS160 phosphorylation by 1.3, 2.5, 1.6, and 2.3 fold at 15, 30, 45, and 60 min, respectively. Treatment of L6 myotubes with UA (10 µM) or RES (100 µM) for 30 min increased AMPK phosphorylation by 1.7 and 5.3 fold, respectively. A combination of UA (10 µM) and RES (100 µM) for 30 min synergistically induced AMPK phosphorylation by a 7.1 fold increase, that is a 76% increase above UA alone and a 26% increase above RES alone (FIG. 1).

Thus, ursolic acid activates the insulin and AMPK signaling pathways in muscle cells and a combination of ursolic acid and resveratrol synergistically activate AMPK in muscle cells. This indicates that UA and RES increase the availability of GLUT 4 transporters that can be translocated to the cell membrane for the uptake of glucose. Since obese and type 2 diabetic individuals have impaired insulin signaling and glucose uptake, phytonutrients, such as ursolic acid and resveratrol, may represent a novel therapeutic approach to improve insulin action and glucose uptake in these individuals.

|  | Mean [3H]-DPM corrected for CYTO B (DPM/mg) | SE | Mean [3H]-2DG per Min per Protein [ ] (pmol/mg/min) | SE | fold change from DMSO |
|---|---|---|---|---|---|
| Basal | 15748.17 | 2808.04 | 185.44 | 33.06 |  |
| DMSO | 10151.45 | 2221.79 | 119.53 | 26.16 | 1.00 |
| Ins 100 nM | 62423.24 | 11708.83 | 598.77 | 29.67 | 5.01 |
| Met 1 mM | 19718.32 | 4818.90 | 232.19 | 56.74 | 1.94 |
| UA 10 uM | 21855.37 | 2248.08 | 257.35 | 26.47 | 2.15 |
| RES 100 uM | 37819.44 | 17343.41 | 244.97 | 55.90 | 2.05 |
| UA + RES | 34038.17 | 8303.67 | 492.64 | 47.44 | 4.12 |

B. Example 2—Synergistic Effects of Resveratrol and Ursolic Acid in Skin-Relevant Systems 1. Materials and Methods Reagents: Ursolic acid (UA), resveratrol (RES), thiazolyl blue tetrazolium bromide (MTT reagent), and an Annexin V/propidium iodide staining kit were obtained from Sigma (St. Louis, Mo.). For in vivo and keratinocyte studies, UA was obtained from Santa Cruz Biotechnology (Santa Cruz, Calif.). Human recombinant TNFα was acquired from R&D Systems (Minneapolis, Minn.). 12-O-tetradecanoylphorbol-13 acetate (TPA) was obtained from LC Laboratories (Woburn, Mass.). The CBA Mouse Th1/Th2/Th17 Cytokine Kit was obtained from Becton Dickinson (Franklin Lakes, N.J.).

Cell culture: HaCaT human keratinocytes were maintained in high glucose DMEM containing 10% fetal bovine serum, 50 U/ml penicillin, and 50 ng/ml streptomycin. MT1/2 mouse skin papilloma cells and Ca3/7 mouse skin carcinoma cells were maintained in Joklik MEM containing 8% FBS, 50 U/ml penicillin, 50 ng/ml streptomycin, 10 µg/ml transferrin, 50 µg/ml gentamicin sulfate, 5 µg/ml insulin, 5 ng/ml EGF, 10 µM o-phosphorylethanolamine, and 10 µM 2-aminoethanol. B16F10 metastatic mouse melanoma cells were grown in DMEM containing 10% FBS, 50 U/ml penicillin, 50 ng/ml streptomycin. A549 human lung adenocarcinoma cells were grown in DMEM/F12 containing 10% FBS, 50 U/ml penicillin, and 50 ng/ml streptomycin. All cells were grown in an incubator at 5% $CO_2$ and 37° C.

Animals and treatment: Female SENCAR mice, 6-7 weeks old, were purchased from NCI Frederick (Frederick, Md.). The dorsal skin of SENCAR mice were shaved and treated topically twice per week for 2 weeks with 200 µL acetone vehicle or 1-3 µmol UA, 1-3 µmol RES, or an equimolar combination of RES and UA. Each treatment was followed 30 minutes later with topical application of 200 µL acetone vehicle or 1-2 µg of the tumor promoter TPA.

In vivo sample collection: Animals were sacrificed 6 hr after the final TPA treatment for Western blotting and 48 hr after the final TPA treatment for histology. For immunohistochemical (IHC) analysis of epidermal proliferation five mice per group were i.p. injected with 100 mg/kg Bromodeoxyuridine (BrdU) in PBS 30 min prior to sacrifice. 1 cm² of mouse skin from treated areas was fixed in formalin and paraffin embedded to be analyzed via IHC.

Immunohistochemistry (IHC): Slides were immunostained with anti-BrdU antibody. The percentage of BrdU-positive cells in the basal cell layer was determined from at least 10 randomly selected sites per slide (5 mice/group). In addition, the epidermal thickness of each skin sample was also measured at 10 random sites for 5 mice/group, using Image Pro-Discovery from Media Cybernetics (Bethesda, Md.).

Western blotting: HaCaT cells were treated with suboptimal doses of RES, UA, or RES+UA and stimulated with 10 ng/ml human tumor necrosis factor alpha (TNFα) for 30 min. Cells were scraped into lysis buffer containing 1% Triton X-100, 0.5% IGEPAL, 0.05 M TrisHCl and 0.1 M NaCl as well as protease/phosphatase inhibitors and 5 mM EDTA. For in vivo studies, whole skin was placed on glass over ice and epidermis was removed by scraping and placed in RIPA buffer with protease/phosphatase inhibitors. Lysates were homogenized and proteins were extracted by centrifugation. Twenty micrograms of protein was separated on Bis-Tris gels and transferred onto PVDF membranes. Membranes were blocked in 5% dry milk or BSA and incubated with primary antibodies overnight at 4° C. Membranes were incubated with corresponding HRP-conjugated secondary antibodies for one hour and developed.

Cytokine analysis: Epidermal samples for each treatment group were pooled and homogenized by mortar and pestle and lysed in 0.05% tween-20 in PBS containing 10 mM PMSF. Proteins were extracted by centrifugation and quantified by Bradford. Equivalent protein amounts (100 or 150 μg) per sample were analyzed in triplicate for levels of inflammatory cytokines, including interleukin-2, interleukin-4, interleukin-6, interleukin-10, interleukin-17A, interferon-γ, and tumor necrosis factor-α using the CBA Mouse Th1/Th2/Th17 Cytokine Kit and an LSR II flow cytometer (Becton Dickinson) according to manufacturer's instructions. Data from each run was normalized to TPA group. Flow cytometry data was generated in the Flow Cytometry Shared Resource Facility.

Luciferase assay for NFKB activity: HaCaT cells were transfected with the NFKB Cignal Reporter Assay Kit from Qiagen, using Attractene transfection reagent, per manufacturer's instructions. Cells were plated at $1.5 \times 10^4$ cells/well in 96 well plates during the transfection. After 16 hr transfection, cells were resupplied with OptiMEM containing 0.5% FBS, 1% non-essential amino acids, 50 U/ml penicillin, and 50 ng/ml streptomycin for 24 hr. Cells were pretreated with various doses of RES or vehicle for 1 hr, followed by UA or vehicle for 1 hr. TNFα at 10 ng/ml was added and cells were incubated for 4 hr. Luminescence of both the TNFα-induced firefly luciferase and the transfection control Renilla luciferase were measured using the Dual-Luciferase Reporter Assay System from Promega and quantified using a Biotek Synergy HT spectrophotometer.

MTT assay for cell viability: Cells were plated at $1.5 \times 10^4$ cells/well on 96-well plates. Cells were pretreated with RES or 0.1% vehicle for 1 hr followed by various doses of UA or 0.1% DMSO vehicle for 24 hr. In the experiment with A549 cells, $5.0 \times 10^3$ cells/well were plated, and cells were treated with UA or 0.1% DMSO for 48 hr after 1 hr pretreatment with RES or vehicle. MTT reagent (0.5 mg/ml) was added, and cells were incubated for an additional 2.5 hr. Media was removed and formazan crystals were dissolved with 100 μl DMSO. Plates were measured at 570 nm with background subtraction at 650 nm, using a Biotek Synergy HT spectrophotometer.

Annexin V/Propidium Iodide staining for apoptotic/necrotic cells: Ca3/7 cells were plated at $2.5 \times 10^5$ cells/well on 6-well plates. Cells were treated with indicated doses of RES, UA, or 0.1% DMSO vehicle for 12 hr. Media and trypsinized cells were collected and spun at 150×g for 3 min, rinsed and spun again, and resuspended in 1× binding buffer containing Annexin V and propidium iodide according to the manufacturer's instructions. Cells were read on an LSR II flow cytometer with dead cells gated out. Flow cytometry data was generated in the Flow Cytometry Shared Resource Facility.

Statistical Analyses: Differences between individual groups were determined by ANOVA. $IC_{50}$ values were calculated with GraphPad Prism. Resistance Reversal (RR) was calculated by dividing the $IC_{50}$ value of the UA+vehicle group by the $IC_{50}$ value of the UA+RES group.

2. Results

RES and UA additively prevent TPA-mediated hyperplasia and proliferation in mouse epidermis. In this study, mice were treated topically with the tumor promoter TPA. This study simulates the promotion phase of the two-stage chemical carcinogenesis model in mice, in which a chemical tumor initiator, usually the PAH 7,12-dimethylbenz(a)anthracene (DMBA), and later promoter are applied to the backs of mice. For these studies, the inventors selected doses of UA which had a moderate effect on TPA-induced changes in preliminary studies. Results revealed that RES at 1, 2, or 3 μmol total dose had no effect, while the same amounts of UA dose-dependently reversed 2 μg TPA-mediated epidermal thickening. The effect of UA was only significantly enhanced by the addition of 2 μmol RES in this study. Also, these doses of RES and UA had limited effect on epidermal proliferation assayed 48 hr after the final TPA treatment. Only 3 μmol of UA alone significantly decreased TPA-induced epidermal proliferation.

The inventors also conducted similar experiments using 1 μg TPA as the promotion stimulus. The lack of impact of RES and UA on 2 μg TPA-induced epidermal proliferation may be due to a saturating effect of this high dose. UA dose-dependently decreased the effect of 1 μg TPA on epidermal thickening. In addition, 2 and 3 μmol doses of RES, while having no effect by themselves, significantly enhanced the anti-hyperplastic effect of equimolar UA doses. Also, UA dose-dependently decreased 1 μg TPA-induced epidermal proliferation, while 2 μmol RES significantly enhanced the effect of 2 μmol UA. The combinations of 2 μmol RES+2 μmol UA and 3 μmol RES+3 μmol UA also returned 1 μg TPA-stimulated epidermal proliferation and hyperplasia back to vehicle control levels. These results indicate the potential of RES to enhance UA's anti-tumor promotion effect.

RES and UA inhibit TPA-mediated inflammatory signaling in mouse epidermis. It was found that RES and UA have an at least additive inhibitory effect on TPA-mediated NFKB signaling in vivo, measured by phosphorylation of the NFKB subunit p65 and total COX-2 levels. Repeat studies demonstrated an additive inhibitory effect of RES and UA on TPA-increased p65 phosphorylation and COX-2 levels.

Figure 2:
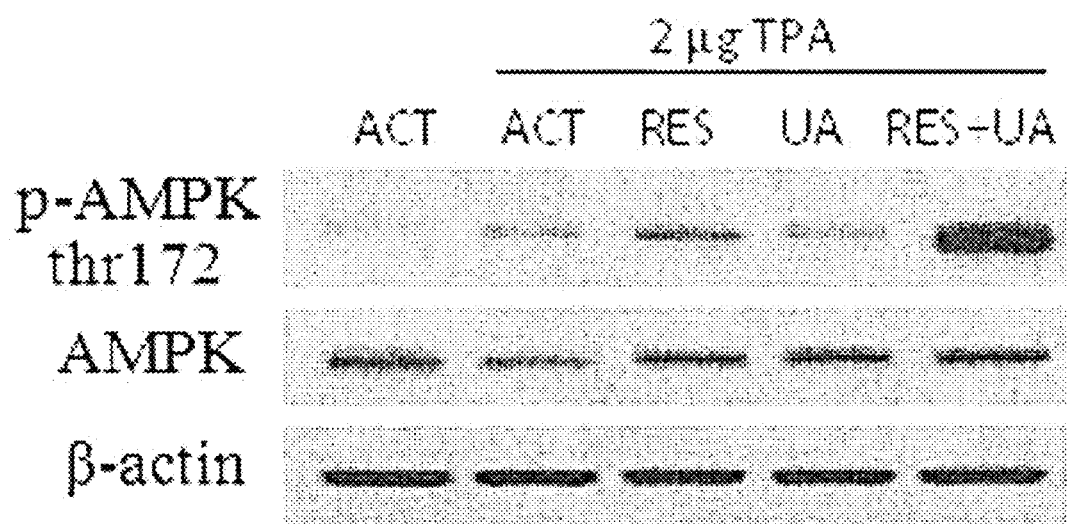
FIG. 2. RES and UA synergistically activate AMPK in a mouse model for skin cancer.

RES and UA synergistically activate AMPK in mouse epidermis. RES and UA have been shown to activate AMPK, which may contribute to their anti-inflammatory, anti-diabetic, and/or anti-cancer effects. It was found that RES and UA synergistically activate AMPK in mouse epidermis (FIG. 2). Repeat experiments also showed the combination of RES and UA activated AMPK in the epidermis. Activation of AMPK may contribute to the decrease in epidermal proliferation, hyperplasia, and inflammatory signaling mediated by the combination of RES and UA. In addition, these results indicate the combination of RES and UA may also synergistically ameliorate diseases inversely associated with AMPK signaling, such as insulin resistance.

RES and UA additively inhibit TNFα-mediated NFKB activity in human keratinocytes. As mentioned before, NFKB activity is important during the tumor promotion phase. The inventors conducted studies in HaCaT human keratinocytes to determine if RES and UA could additively or synergistically inhibit NFKB activity. Cells were pretreated with doses of RES (100 and 200 μM) and UA (10 and 20 μM), which had a moderate effect on TNFα-induced NFKB activity in preliminary experiments (measured by phosphorylation of active subunit p65). Combinations of RES and UA generally had an additive inhibitory effect on TNFα-mediated p65 phosphorylation.

Downstream NFKB transcriptional activity was also analyzed via luciferase reporter gene assay. For combination experiments, UA doses which had a moderate effect on TNFα-induced NFKB activity were selected. UA dose-dependently decreases TNFα-stimulated NFKB activity, and this effect is at least partially reversed with 100 μM RES. In another experiment, increasing doses of RES were combined with 20 μM UA. At higher doses of RES (100 and 200 μM), which partially inhibited NFKB themselves, the combination of RES and UA has an additive effect. The inventors observed an antagonistic effect of lower doses of RES (50 μM) with UA.

Figures 3A, 3B:
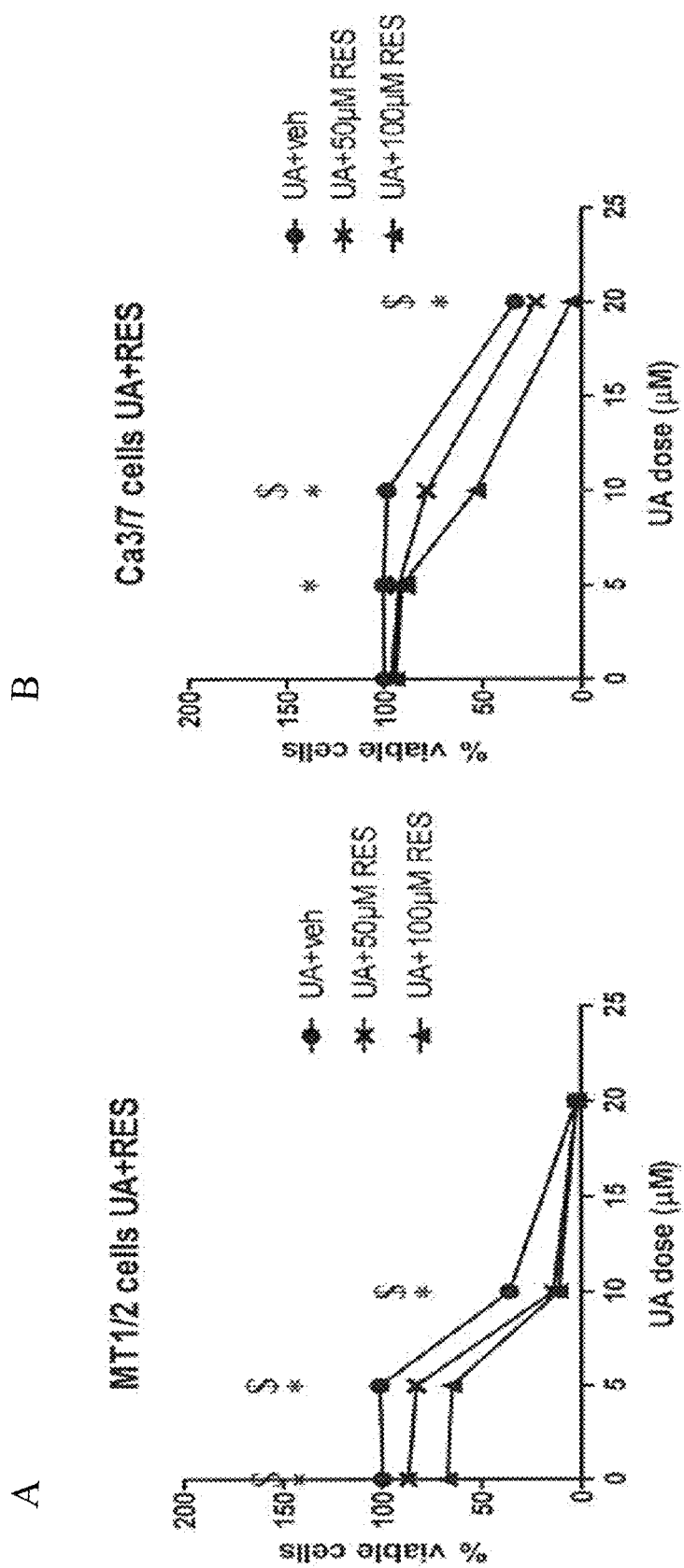
FIGS. 3A-B. RES sensitizes MT1/2 mouse papilloma cells and Ca3/7 mouse squamous carcinoma cells to UA.
Figure 4:
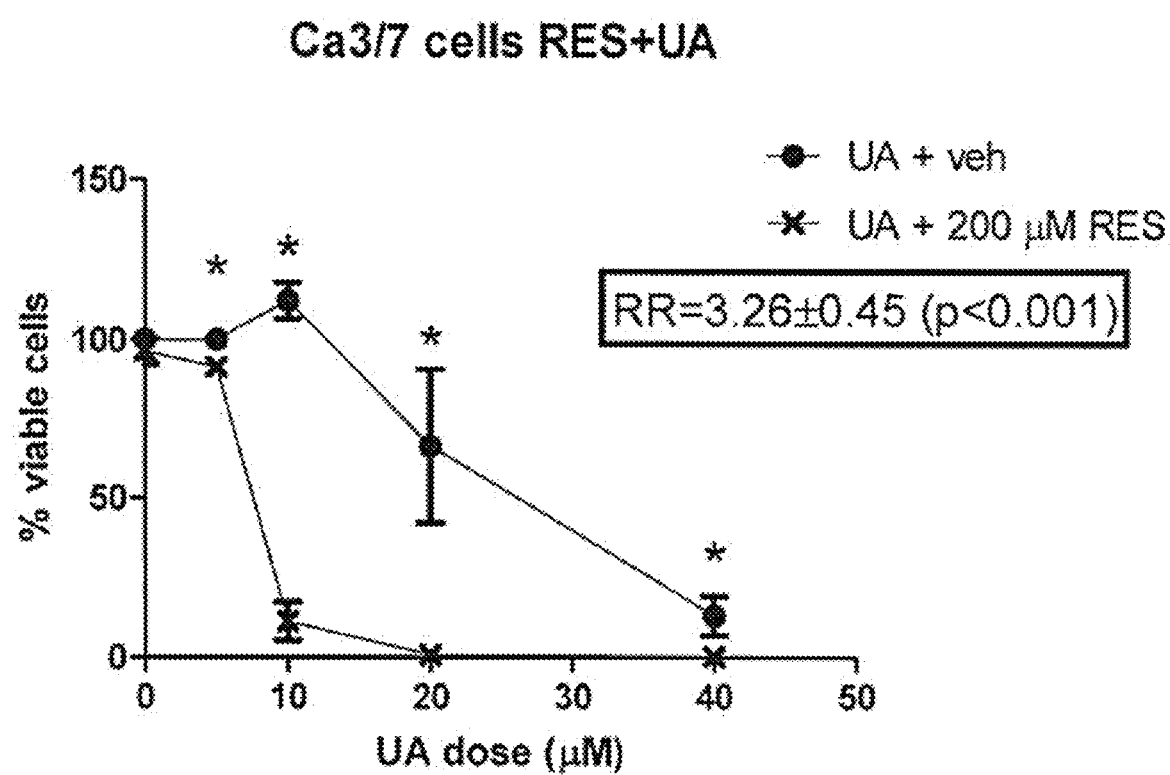
FIG. 4. A higher concentration of RES increases the sensitivity of Ca3/7 cells to UA (n=3, * indicates p<0.05).
Figure 5:
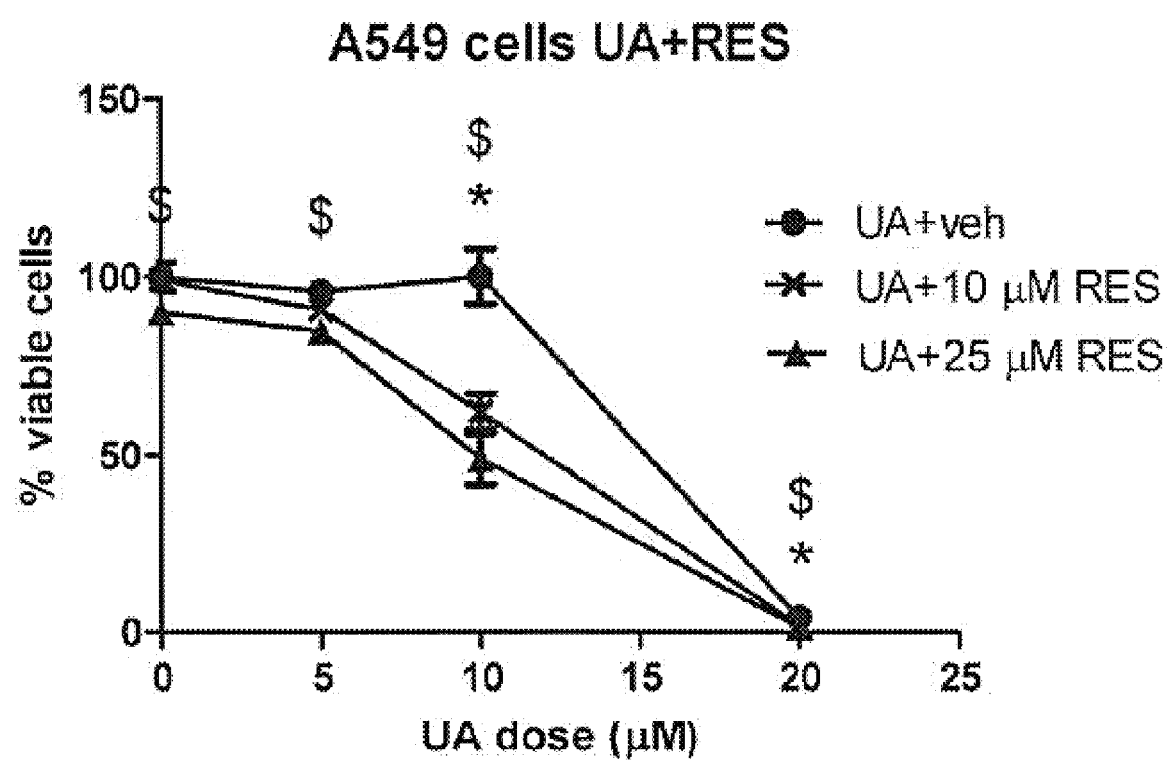
FIG. 5. UA and RES synergistically inhibit viability of human lung adenocarcinoma cell line A549 (n=3, * indicates p<0.05 between UA+veh and UA+10 µM RES, $ indicates p<0.05 between UA+veh and UA+25 µM RES).

RES enhances the cytotoxic effects of UA in skin cancer cell lines. In both MT1/2 mouse papilloma cells and Ca3/7 mouse squamous carcinoma cells, increasing doses of RES lowered the $IC_{50}$ values of UA. The fold by which the $IC_{50}$ is decreased is indicated by resistance reversal (FIGS. 3A-B), and is dose dependently enhanced by RES. In another study, the ability of 200 μM RES to enhance UA-mediated growth suppression was tested. RES strongly and significantly synergized with UA (FIG. 4). The synergistic effects of RES and UA in the Ca3/7 cell line were confirmed by flow cytometry, which showed an enhancement of mixed apoptotic/necrotic cell death. In addition, the synergistic effects of RES and UA were also evident in the highly metastatic mouse melanoma cell line B16F10 as well as in the human lung adenocarcinoma cell line A549 (FIG. 5).

The invention claimed is:

1. A method of decreasing obesity in a human, the method comprising:
   eating, one or more times per day, an effective amount of a nutritional supplement comprising ursolic acid and resveratrol in a ratio of ursolic acid to resveratrol of 3:1 to 1:3 to decrease obesity in the human;
   continuing eating an effective amount of the nutritional supplement for multiple days; and
   decreasing obesity in the human;
   wherein the nutritional supplement is formulated as a tablet, a capsule, a concentrate, a powder, a drink, or a food, and
   is eaten in addition to food in a normal diet.

2. The method of claim 1, wherein the effective amount of the nutritional supplement comprises 50 to 600 mg of ursolic acid.

3. The method of claim 1, wherein the effective amount of the nutritional supplement comprises 200 mg of ursolic acid.

4. The method of claim 1, wherein the effective amount of the nutritional supplement comprises 50 to 600 mg resveratrol.

5. The method of claim 1, wherein the effective amount of the nutritional supplement comprises 600 mg of resveratrol.

6. The method of claim 1, wherein the effective amount of the nutritional supplement comprises 200 mg of ursolic acid and 600 mg of resveratrol.

7. The method of claim 1, wherein the effective amount of the nutritional supplement comprises 100 mg of ursolic acid and 200 mg of resveratrol.

8. The method of claim 1, wherein the nutritional supplement comprises one or more of a preserving, an emulsifying, or a dispersing agent.

9. The method of claim 1, wherein the nutritional supplement comprises one or more of a filler or extender, a binder, a humectant, a disintegrating agent, solution retarder, absorption accelerator, wetting agent, an adsorbent, lubricant, or buffering agent.

10. The method of claim 9, wherein the filler is starch, lactose, sucrose, mannitol, or silicic acid.

11. The method of claim 9, wherein the binder is carboxymethylcellulose, alginates, gelatin, polyvinylpyrrolidone, sucrose, or acacia.

12. The method of claim 9, wherein the humectant is glycerol.

13. The method of claim 9, wherein the disintegrating agent is agar-agar, calcium carbonate, potato or tapioca starch, alginic acid, complex silicates, or sodium carbonate.

14. The method of claim 9, wherein the solution retarder is paraffin.

15. The method of claim 9 wherein the wetting agent is cetyl alcohol or glycerol monostearate.

16. The method of claim 9, wherein the lubricant is talc, calcium stearate, magnesium stearate, solid polyethylene glycols, sodium lauryl sulfate, or mixtures thereof.

17. The method of claim 9, wherein the nutritional supplement is a baked good, chocolate, caramel, cookie, or bar.

18. The method of claim 1, wherein the nutritional supplement is a baked good, chocolate, caramel, cookie, or bar.

* * * * *